US012012435B2

(12) United States Patent
Grijpstra et al.

(10) Patent No.: US 12,012,435 B2
(45) Date of Patent: Jun. 18, 2024

(54) FimH MUTANT, COMPOSITIONS THEREWITH AND USE THEREOF (71) Applicant: Janssen Pharmaceuticals, Inc., Titusville, NJ (US)

(72) Inventors: Jan Grijpstra, Beesd (NL); Marleen Eveline Weerdenburg, Uithoorn (NL); Jeroen Geurtsen, Vleuten (NL); Cristhina Kellen Fae, Mainz (DE); Jakob Louris Feitsma, Utrecht (NL)

(73) Assignee: JANSSEN PHARMACEUTICALS, INC., Titusville, NJ (US)

( * ) Notice: Subject to any disclaimer, the term of this patent is extended or adjusted under 35 U.S.C. 154(b) by 4 days.

(21) Appl. No.: 17/814,966

(22) Filed: Jul. 26, 2022

(65) Prior Publication Data
US 2023/0049056 A1 Feb. 16, 2023

Related U.S. Application Data (62) Division of application No. 17/150,025, filed on Jan. 15, 2021, now Pat. No. 11,421,003.

(30) Foreign Application Priority Data

Jan. 16, 2020 (EP) .................... 20152217

(51) Int. Cl.
*A61K 39/02* (2006.01)
*A61K 39/108* (2006.01)
*C07K 14/195* (2006.01)
*C07K 14/245* (2006.01)
*C07K 16/12* (2006.01)

(52) U.S. Cl.
CPC .......... *C07K 14/195* (2013.01); *A61K 39/025* (2013.01); *A61K 39/0258* (2013.01); *A61K 39/0266* (2013.01); *C07K 14/245* (2013.01); *C07K 16/1232* (2013.01)

(58) Field of Classification Search
None
See application file for complete search history.

(56) References Cited

U.S. PATENT DOCUMENTS

| | | |
|---|---|---|
| 4,436,727 A | 3/1984 | Ribi |
| 4,866,034 A | 9/1989 | Ribi |
| 4,877,611 A | 10/1989 | Cantrell |
| 4,912,094 A | 3/1990 | Myers |
| 4,987,237 A | 1/1991 | Myers |
| 5,057,540 A | 10/1991 | Kensil |
| 5,191,072 A | 3/1993 | Hasegawa |
| 5,370,872 A | 12/1994 | Cryz |
| 5,593,969 A | 1/1997 | Kamireddy |
| 5,750,110 A | 5/1998 | Prieels |
| 6,299,884 B1 | 10/2001 | Van Nest |
| 6,451,325 B1 | 9/2002 | Van Nest |
| 6,491,919 B2 | 12/2002 | Crane |
| 6,500,434 B1 | 12/2002 | Langermann |
| 6,676,958 B2 | 1/2004 | Gerber |
| 6,737,063 B2 | 5/2004 | Langermann |
| 6,759,241 B1 | 7/2004 | Hone |
| 7,357,936 B1 | 4/2008 | Garcon |
| 8,168,195 B2 | 5/2012 | Szu |
| 8,722,064 B2 | 5/2014 | Reed |
| 9,017,698 B2 | 4/2015 | Eldridge |
| 9,149,521 B2 | 10/2015 | Eldridge |
| 9,149,522 B2 | 10/2015 | Eldridge |
| 9,415,097 B2 | 8/2016 | Eldridge |
| 9,415,101 B2 | 8/2016 | Eldridge |
| 9,504,743 B2 | 11/2016 | Eldridge |
| 9,700,612 B2 | 7/2017 | Kowarik |
| 10,441,647 B2 | 10/2019 | Kowarik |
| 10,456,462 B2 | 10/2019 | Langedijk |
| 11,229,694 B2 | 1/2022 | Langedijk et al. |
| 11,421,003 B2 | 8/2022 | Grijpstra |
| 11,725,028 B2 | 8/2023 | Grijpstra |
| 2002/0150587 A1 | 10/2002 | Langermann |
| 2003/0138449 A1 | 7/2003 | Langermann |
| 2003/0199071 A1 | 10/2003 | Solomon |
| 2010/0310602 A1 | 12/2010 | Reed |
| 2011/0206758 A1 | 8/2011 | Vandepapeliere |
| 2015/0056224 A1 | 2/2015 | Dubensky, Jr. |
| 2015/0238588 A1 | 8/2015 | Kowarik |
| 2019/0275135 A1 | 9/2019 | Poolman |
| 2021/0221856 A1 | 7/2021 | Grijpstra |
| 2022/0125912 A1 | 4/2022 | Langedijk et al. |
| 2022/0220159 A1 | 7/2022 | Grijpstra |

FOREIGN PATENT DOCUMENTS

| | | |
|---|---|---|
| EP | 0399843 | 11/1990 |
| EP | 0761231 A1 | 3/1997 |
| EP | 0671948 B1 | 8/1997 |

(Continued)

OTHER PUBLICATIONS

Sarshar et al. Antibiotics 9: 397: p. 1 of 16-16 of 16, 2009.
Bouchaert et al., (2005) 55:2 441-455.
Chen et al., (2009) PNAS 106:52, 22439-22444.
Adjuvants—Immunotherapy & Vaccine Development, Avanti Polar Lipids, Inc., downloaded from web page: http://www.avantilipids.com/divisions/adjuvants, Download date: Sep. 11, 2019, original posting date: unknown, 4 pages.
Alving et al., "Adjuvants for Human Vaccines", Current Opinion in Immunology, vol. 24, No. 3, pp. 310-315 (Jun. 2012).

(Continued)

*Primary Examiner* — S. Devi
(74) *Attorney, Agent, or Firm* — Ice Miller LLP (57) ABSTRACT

Polypeptides comprising a FimH lectin domain comprising an amino acid mutation that causes the FimH lectin domain to be in the low affinity conformation for mannose are described. Pharmaceutical compositions which comprise such polypeptides and methods of stimulating an immune response in a subject in need thereof by administration of the polypeptide are further described.

15 Claims, 1 Drawing Sheet
Specification includes a Sequence Listing.

(56) References Cited

FOREIGN PATENT DOCUMENTS

| | | |
|---|---|---|
| EP | 0971739 B1 | 10/2004 |
| EP | 1126876 B1 | 3/2007 |
| EP | 1194166 B1 | 12/2007 |
| EP | 1385541 B1 | 6/2008 |
| GB | 2220211 A | 1/1990 |
| WO | 0204496 A2 | 1/2002 |
| WO | 2002102974 | 12/2002 |
| WO | 2006116423 A2 | 11/2006 |
| WO | 2006119987 A2 | 11/2006 |
| WO | 2007109812 A2 | 9/2007 |
| WO | 2007109813 A1 | 9/2007 |
| WO | 2009104074 A2 | 8/2009 |
| WO | 2013119856 A1 | 8/2013 |
| WO | 2015124769 A1 | 8/2015 |
| WO | 2016183501 | 11/2016 |
| WO | 2017035181 A1 | 3/2017 |
| WO | 2021123360 A1 | 6/2021 |

OTHER PUBLICATIONS

Apicella et al, "Isolation and Characterization of Lipopolysaccharides, Lipoogliosaccharides, and Lipid A," Methods n Enzymology, vol. 235, pp. 242-252 (1994).

Baliban et al, "Development of glycoconjugate vaccine to prevent invasive *Salmonella typhimurium* infections in sub-Saharan Africa," PLOS Neglected Tropical Diseases, vol. 11, No. 4, p. e0005493 (Apr. 2017) 27 pages.

Barnhart et al, "Chaperone-Subunit-Usher Interactions Required for Donor Strand Exchange during Bacterial Pilus Assembly," Journal of Bacteriology, vol. 185, No. 9, pp. 2723-2730 (May 2003).

Barnhart et al, "PapD-like chaperones provide the missing information for folding of pilin proteins," Proceedings of the National Academy of Sciences of the United States of America, vol. 97, No. 14, pp. 7709-7714 (Jul. 2000).

Boudeau et al, "Invasive Ability of an *Escherichia coli* Strain Isolated from the Ileal Mucosa of a Patient with Crohn's Disease," Infection and Immunity, vol. 67, No. 9, pp. 4499-4509 (Sep. 1999).

Brumbaugh et al, "Preventing urinary tract infection: progress toward an effective *Escherichia coli* vaccine," Expert Review of Vaccines, vol. 11, No. 6, pp. 663-676 (Jun. 2012).

Carter et al, "A structure-function approach to optimizing TLR4 ligands for human vaccines," Clinical & Translational Immunology, vol. 5, p. e108 (2016) 8 pages.

Choudhury et al, "X-ray structure of the FimC-FimH Chaperone-Adhesin Complex from Uropathogenic *Escherichia coli*," Science, vol. 285, pp. 1061-1066 (Aug. 1999).

Conte et al, "Adherent-invasive *Escherichia coli* (AIEC) in pediatric Crohn's disease patients: phenotypic and genetic pathogenic features," BMC Research Notes, vol. 7, p. 748 (2014).

Cryz et al, "Synthesis and characterization of a polyvalent *Escherichia coli* 0-polysaccharide-toxin A conjugate vaccine," Vaccine, vol. 13, No. 5, pp. 449-453 (1995).

Desilets et al, "Genome-based Definition of an Inflammatory Bowel Disease-associated Adherent-Invasive *Escherichia coli* Pathovar," Inflammatory Bowel Diseases, vol. 22, pp. 1-12 (2015).

Fattom et al, "Epitopic overload at the site of injection may result in suppression of the immune response to combined capsular polysaccharide conjugate vaccines," Vaccine, vol. 17, pp. 126-133 (1999).

Ghosh Arunita et al: "Incidence of multidrug resistance, pathogenicity island markers, and pathoadaptive FimH mutations in uropathogenic *Escherichia coli* isolated from asymptomatic hospitalized patients", Folia Microbiologica, Springer Netherlands, NL, vol. 64, No. 4, Mar. 5, 2019 (Mar. 5, 2019), pp. 587-600, XP036833816, ISSN0015-5632, DOI: 10.1007/S12223-019-00685-4.

Greenspan et al. Nature Biotechnology 17: 936-937, 1999.

Gregg et al, "Rationally Designed TLR4 Ligands for Vaccine Adjuvant Discovery," MBio, vol. 8, No. 3, pp. e00492-300517(2017).

Ho et al, "Preclinical Laboratory Evaluation of a Bivalent *Staphylococcus aureus* Saccharide-Exotoxin A Protein Conjugate Vaccine," Human Vaccines, vol. 2, No. 3, pp. 89-89 (2006).

Huttner et al, "Safety, immunogenicity, and preliminary clinical efficacy of a vaccine against extraintestinal pathogenic *Escherichia coli* in women with a history of recurrent urinary tract infection: a randomised, single-blind, placebo-controlled phase 1b trial," The Lancet Infectious Diseases, vol. 17, pp. 3099-30108, (2017).

Ihssen et al, "Production of glycoprotein vaccines in *Escherichia coli*," Microbial Cell Factories, vol. 9, p. 61 (2010).

Reton et al, "Adjuvants containing natural and synthetic Toll-like receptor 4 ligands," Expert Review of Vaccines, vol. 12, pp. 793-807 (2013).

Johnson et al, "3-O-Desacyl Monophosphoryl Lipid A Derivatives: Synthesis and Immunostimulant Activities," Journal of Medical Chemistry, vol. 42, pp. 4640-4649 (1999).

Kensil et al, "Structural and Immunogical Characterization of the Vaccine Adjuvant QS-21," Vaccine Design: The Subunit and Adjuvant Approach, pp. 525-541 (1995).

Kisiela et al. 2013 (Conformations inactivation induces immunogenicity of the receptor-binding pocket of a bacterial adhesion; PNAS 110 (47): 19089-19094) (Year: 2013).

Langermann et al, "Prevention of Mucosal *Escherichia coli* Infection by FimH-Adhesin-Based Systemic Vaccination," Science, vol. 276, pp. 607-611 (1997).

Langermann et al. 2000 (Vaccination with FimH adhesion Protects Cynomolgus Monkeys from Colonization and Infection by Uropathogenic *Escherichia coli*; The Journal of Infectious Diseases 181:774-8) (Year: 2000).

Lazar et al. Mol. Cellular Biol. 8: 1247-1252, 1988.

Lukac et al, "Toxoid of *Pseudomonas aeruginosa* Exotoxin A Generated by Deletion of an Active-Site Residue," Infection and Immunity, vol. 56, No. 12, pp. 3095-3098 (1988).

Martinez-Medina et al, "*Escherichia coli* in chronic inflammatory bowel diseases: An update on adherent invasive *Escherichia coli* pathogenicity," World Journal of Gastrointestinal Pathophysiology, vol. 5, No. 3, pp. 213-227 (2014).

Masson et al, "Calcium phosphate: a substitute for aluminum adjuvants?" Expert Review of Vaccines, vol. 16, pp. 289-299 (2017).

Meloni et al, "Simplified low-cost production of 0-antigen from *Salmonella typhimurium* Generalized Modules for Membrane Antigens (GMMA)," Journal of Biotechnology, vol. 198, pp. 46-52 (2015).

Micoli et al, "A scalable method for 0-antigen purification applied to various *Salmonella serovars*," Analytical Biochemistry, vol. 434, pp. 136-145 (2013).

Morrison et al. Curr. Opin. Chem. Biol. 5: 302-307, 2001.

Nash et al, "Genome sequence of adherent-invasive *Escherichia coli* and comparative genomic analysis with other *E. coli* pathotypes," BioMed Central Genomics, vol. 11, No. 667 (2010), 15 pages.

O'Brien et al, "A mucosal imprint left by prior *Escherichia coli* bladder infection sensitizes to recurrent disease," Nature Microbiology, vol. 2, No. 16196 (2016) 10 pages.

Pawlowski et al, "Preparation of pneumococcal capsular polysaccharide-protein conjugate vaccines utilizing new fragmentation and conjugation technologies," Vaccine, vol. 18, No. 18, pp. 1873-1885 (2000).

Pearl Magala et al: "RMSD analysis of structures of the bacterial protein FimH identifies five conformations of its lectin domain", Proteins: Structure, Function, and Bioinformatics, vol. 88, No. 4, Oct. 17, 2019 (Oct. 17, 2019), pp. 593-603, XP055706802, US ISSN: 0887-3585, DOI: 10.1002/prot.25840.

Petrovsky et al, "AdvaxTM, a novel microcrystalline polysaccharide particle engineered from delta inulin, provides robust adjuvant potency together with tolerability and safety," Vaccine, vol. 33. pp. 5920-5926 (2015).

R. Stenutz et al., "The structures of *Escherichia coli* O-polysaccharide antigens", FEMS Microbiol. Rev., May 2006, vol. 30, No. 3, pp. 382-403.

Rabbani et al, "Expression of the carbohydrate recognition domain of FimH and development of a competitive binding assay," Analytical Biochemistry, vol. 407, pp. 188-195 (2010).

(56) References Cited

OTHER PUBLICATIONS

Raetz et al, "Lipopolysaccharide Endotoxins," Annual Review of Biochemistry, vol. 71, pp. 635-700 (2002).

Raetz, "Bacterial Endotoxins: Extraordinary Lipids That Activate Eucaryotic Signal Transduction," Journal of Bacteriology, vol. 175, No. 18, pp. 5745-5753 (1993).

Reed et al, "Key roles of adjuvants in modern vaccines," Nature Medicine, vol. 19, No. 12, pp. 1597-1608 (2013).

Reed et al, "The science of vaccine adjuvants: advances in TLR4 ligand adjuvants," Current Opinion in Immunology, vol. 41, pp. 85-90 (2016).

Robbins et al, "Synthesis, characterization, and immunogenicity in mice of Shigella sonnei O-specific oligosaccharide-core-protein conjugates," Proceedings of the National Academy of Sciences of the United States of America, vol. 106, No. 19, pp. 7974-7978 (2009).

Rodriquez et al. 2013 (Allosteric Coupling in the Bacterial Adhesive Protein FimH; J of Biol Chem 288(33): 24128-24139 (Year: 2013).

Rondini et al, "Design of glycoconjugate vaccines against invasive African S. Typhimurium," Infection and Immunity, vol. 83, pp. 996-1007 (2015).

Rudinger J. In: Peptide Hormones. (Ed) JA Parsons, University Park Press, pp. 1-7, 1976.

Russo et al, "Medical and economic impact of extraintestinal infections due to *Escherichia soli*: focus on an Increasingly important endemic problem," Microbes and Infection, vol. 5, pp. 449-456 (2003).

Saraswat et al, "Preparative Purification of Recombinant Proteins: Current Status and Future Trends," BioMed Research International, Article ID No. 312709, pp. 1-18 (2013).

Sauer et al, "Catch-bond mechanism of the bacterial adhesin FimH," Nature Communications, vol. 7, Article ID No. 10738, pp. 1-13 (2016).

Schembri et al, "Identification of a 13-kDa protein associated with the polyhydroxylkanoic acid granules from *Acinetobacter* spp.," Federation of European Microbiological Societies Microbiology Letters, vol. 133, pp. 277-283 (1995).

Schwartz et al, "Positively selected FimH residues enhance virulence during urinary tract infection by altering FimH conformation," Proceedings of the National Academy of Sciences of the United States of America, vol. 110, No. 39, pp. 15530-15537 (2013).

Skolnick et al. Trends in Biotechnology, 18: 34-39, 2000.

Stefanetti et al, "Click Chemistry Applied to the Synthesis of *Salmonella typhimurium* 0-Antigen Glycoconjugate Vaccine on Solid Phase with Sugar Recycling," Bioconjugate Chemistry, vol. 26, pp. 2507-2513 (2015).

Stefanetti et al, "Impact of conjugation chemistry on the immunogenicity of S. Typhimurium conjugate vaccines," Vaccine, vol. 32, pp. 6122-6129 (2014).

Stefanetti et al, "Sugar-Protein Connectivity Impacts on the Immunogenicity of Site-Selective *Salmonella* 0-Antigen Glycoconjugate Vaccines," Angewandte Chemie International Edition, vol. 54, pp. 1-6 (2015).

Stoute et al, "A Preliminary Evaluation of a Recombinant Circumsporozoite Protein Vaccine Against Plasmodium Falciparum Malaria," The New England Journal of Medicine, vol. 336, pp. 86-91 (1997).

Ulrich et al, "Monophosphoryl Lipid A as an Adjuvant," Vaccine Design: The Subunit and Adjuvant Approach, pp. 195-524(1995).

Woodward et al, "In vitro bacterial polysaccharide biosynthesis: defining the functions of Wzy and Wzz," Nature Chemical Biology, vol. 6, No. 6, pp. 418-423 (2010).

Zhu et al, "QS-21: A Potent Vaccine Adjuvant," Natural Products Chemistry & Research, vol. 3, No. 4, p. 1000e113 (2015).

FimH MUTANT, COMPOSITIONS THEREWITH AND USE THEREOF

CROSS-REFERENCE TO RELATED APPLICATION

This application is a divisional application claiming priority to U.S. application Ser. No. 17/150,025 filed Jan. 15, 2021, now U.S. Pat. No. 11,421,003, issued on Aug. 23, 2023, which claims priority to European Patent Application No. 20152217.4 filed Jan. 16, 2020, the disclosures of which are incorporated herein by reference in their entireties.

REFERENCE TO SEQUENCE LISTING SUBMITTED ELECTRONICALLY

The contents of the electronic sequence listing (004852_117US2.xml; Size: 8,530 bytes; and Date of Creation: Aug. 26, 2022) is herein incorporated by reference in its entirety.

FIELD OF THE INVENTION

This invention relates to the fields of medical microbiology, immunology and vaccines. In particular, the invention relates to polypeptides comprising a FimH lectin domain comprising an amino acid mutation that causes the FimH lectin domain to be in a conformation with low affinity for mannose and inducing high levels of antibody-mediated inhibition of adhesion of E. coli to bladder epithelial cells upon administration to a subject. Furthermore, the invention relates to compositions which comprise such polypeptides and to methods of stimulating an immune response in a subject in need thereof by administration of the immunogenic polypeptide.

BACKGROUND OF THE INVENTION

Strains of E. coli responsible for extra-intestinal infections are genetically distinct from those that cause intestinal disease and have been termed extra-intestinal pathogenic E. coli (ExPEC). ExPEC are the most common enteric Gram-negative organisms to cause extra-intestinal infection in the ambulatory, long-term-care, and hospital settings. Typical extra-intestinal infections due to E. coli include urinary tract infection (UTI), diverse intra-abdominal infections (IAI), pneumonia, surgical site infection, meningitis, intravascular device infection, osteomyelitis, and soft tissue infections, any of which can be accompanied by bacteremia. E. coli is a leading cause of severe sepsis and it is responsible for high morbidity and mortality rates.

ExPEC, as other members of the Enterobacteriaceae family, produces type I fimbriae, which aid in the attachment to mucosal epithelial surfaces. These type I fimbriae are hair-like structures which emanate from the surface members of the Enterobacteriaceae family. The major component of Type I fimbriae is repeating subunits of FimA arranged in a right-handed helix to form a filament approximately 1 μm in length and 7 nm in diameter with a central axial hole (Brinton, 1965). Along with FimA as the major subunit, the fimbrial filament also contains FimF, FimG and FimH as minor protein subunits. The minor protein subunit FimH is a mannan-binding adhesin that promotes adherence of Type I-fimbriated bacteria to mannose-containing glycoproteins on eukaryotic cell surfaces and represents a family of proteins which bind to various targets, including mannan and fibronectin. Immune electron microscopy studies have revealed that FimH is strategically placed at the distal tips of Type I fimbriae where it appears to be complexed with FimG, forming a flexible fibrillum structure, and is also placed longitudinally at various intervals along the filament.

The FimH adhesin protein has been shown to induce protection when used as vaccine in various pre-clinical models against UTI (Langermann S, et al., 1997, Science, 276: 607-611; Langermann S, et al., 2000, J Infect Dis, 181: 774-778; O'Brien V P et al., 2016, Nat Microbiol, 2:16196). In 1999, Medimmune brought a FimH-containing subunit vaccine to phase II trials, but development of the vaccine was discontinued in 2003 for lack of efficacy in prevention of UTIs (see, e.g., Brumbaugh A R and Mobley H L T, 2012, Expert Rev Vaccines, 11: 663-676). Nevertheless, the company Sequoia Sciences appears to be currently clinically developing a vaccine for recurrent UTIs, the vaccine consisting of the FimH protein complexed with the FimC protein and combined with a new adjuvant formulation. The company reports that this vaccine was highly immunogenic and well-tolerated and may reduce the frequency of UTI, although safety and efficacy still need to be established (hypertext://www.sequoiasciences.com/uti-vaccine-program).

It has been shown that during E. coli infection, the lectin domain of the adhesin FimH, that binds to mannosylated receptors, can adopt two distinct conformations: low-affinity for mannose (tense) and high-affinity for mannose (elongated/relaxed) (Kalas et al, 2017, Sci Adv 10; 3(2)). The low affinity conformation promotes bacterial motility and colonization of new tissues. The high-affinity conformation ensures tight bacterial adhesion under the mechanical forces of urine excretion (Kalas et al, 2017 supra). Furthermore, antibodies against low-affinity variant were shown to block bacterial binding to uroepithelial cells and reduce CFU counts in the bladder (Tchesnokoca, 2011 Infect Immun. 79(10):3895-904; Kisiela, 2013 Proc Natl Acad Sci, 19; 110(47):19089-94).

WO02102974 describes a number of FimH mutants that all comprise an amino acid modification in the canyon region of the molecule. Specifically, WO02102974 describes variants wherein mannose interacting residues in the binding pocket are mutated. This location of the mutation is selected because it would keep the FimH mutant in a more open conformation and thereby expose epitopes that are poorly accessible in the wild-type protein. However, to date, to the best of our knowledge, none of these mutants have been further pursued as vaccine candidates. In clinical trials, only wild-type FimH has been used. Thus, there remains a need in the art for vaccines that can induce highly inhibitory antibodies against bacterial infections caused by E. coli.

SUMMARY OF THE INVENTION

In a first aspect, the invention provides for a polypeptide comprising a FimH lectin domain, wherein the FimH lectin domain comprises an amino acid selected from the group consisting of valine (V), isoleucine (I), leucine (L), glycine (G), methionine (M), and alanine (A) at the position that corresponds to position 144 in SEQ ID NO: 1.

In a second aspect, the invention provides for a complex comprising a full length-FimH polypeptide according to the invention and FimC (FimCH).

In a third aspect, the invention provides a polynucleotide encoding a polypeptide according to the invention.

In a fourth aspect, the invention provides for a pharmaceutical composition comprising a polypeptide according to the invention, a complex according to the invention, or a polynucleotide according to the invention.

In a fifth aspect, the invention provides for a polypeptide according to the invention, a complex according to the invention, a polynucleotide according to the invention, or a pharmaceutical composition according to the invention for use as a medicament.

In a sixth aspect, the invention provides for a polypeptide according to the invention, a complex according to the invention, a polynucleotide according to the invention, or a pharmaceutical composition according to the invention for use in inducing an immune response against a bacterium of the family of Enterobacteriaceae. The invention further relates to a method for treating or preventing an enterobacillus-related condition in a subject in need thereof, the method comprising administering an effective amount of a polypeptide according to the invention, a polynucleotide according to the invention or a pharmaceutical composition according to the invention.

In a seventh aspect, the invention provides for a vector comprising the polynucleotide according to the invention.

In an eighth aspect, the invention further provides for a method for producing a polypeptide comprising expressing the polypeptide from a recombinant cell containing the polynucleotide of the invention and/or the vector of the invention, optionally the method further comprises recovering the polypeptide which is optionally followed by formulation into a pharmaceutical composition of the polypeptide.

BRIEF DESCRIPTION OF THE DRAWINGS

FIG. 1: Levels of FimH serum antibodies (total IgG) induced by different FimH variants. Wistar rats (n=2) received 4 intramuscular immunizations at day 0, 7, 10 and 18 with 60 ug/dose of the different FimH variants combined with a non-Freund's adjuvant (Speedy-rat model, Eurogentec). Levels of anti-FimH antibodies were measured by ELISA pre-immunization (day 0, open circles) and post-immunization (day 28, closed circles). Data represents mean of duplicate serum samples from 2 animals/group. Antibody titers (EC50) were calculated based on a 4-parameter logistic regression model fitted on a 12-step dilution curve.

DETAILED DESCRIPTION OF THE INVENTION

The invention provides for a novel polypeptide comprising a FimH lectin domain wherein the FimH lectin domain is "locked" in a conformation with low affinity for mannose, also referred to herein as the 'low affinity conformation'. The present invention is based in part on the observation that FimH antigen in the low affinity for mannose conformation is capable of inducing antibodies that can inhibit mannoside-mediated adhesion. These antibodies are highly inhibitory and have an enhanced effect in preventing or treating bacterial infections. It was found herein that a FimH lectin domain with an F144V mutation has a surprisingly good combination of desirable properties that makes it very suitable for use in vaccines against UTI, e.g. to prevent or reduce recurrent UTI.

Accordingly, in a first aspect, the invention provides for a polypeptide, preferably an immunogenic polypeptide, comprising a FimH lectin domain, wherein the FimH lectin domain comprises an amino acid selected from the group consisting of valine (V), isoleucine (I), leucine (L) glycine (G), methionine (M), and alanine (A), at the position that corresponds to position 144 in SEQ ID NO: 1.

The amino acid position 144 refers to position 144 in the reference amino acid sequence of the FimH lectin domain of SEQ ID NO: 1. In amino acid sequences of the invention other than SEQ ID NO: 1, preferably, the amino acid position 144 is present in an amino acid position corresponding to the position 144 in SEQ ID NO: 1, preferably in a ClustalW (1.83) sequence alignment using default settings. The skilled person will know how to identify corresponding amino acid positions in FimH lectin domain amino acid sequences other than SEQ ID NO: 1 using amino acid sequence alignment algorithms as defined hereinabove.

In one embodiment, the polypeptide comprising a FimH lectin domain according to the invention comprises a mutation that causes the FimH lectin domain to be in the low affinity for mannose conformation. In one embodiment, the polypeptide comprising a FimH lectin domain according to the invention has been mutated at a position that corresponds to position 144 in SEQ ID NO: 1. The mutation can be any one of a deletion, addition or substitution of a single amino acid residue. Preferably, the mutation is a substitution of a single amino acid residue. The mutation is preferably a substitution of an amino acid residue that corresponds to position 144 in SEQ ID NO: 1. Preferably, the mutation is a substitution of a phenylalanine (F) amino acid residue at a position corresponding to position 144 in SEQ ID NO: 1. In the polypeptide comprising a FimH lectin domain of the invention the position that corresponds to position 144 in SEQ ID NO: 1 is preferably substituted for an amino acid selected from the group consisting of valine (V), isoleucine (I), leucine (L), glycine (G), methionine (M), and alanine (A). The terms 'mutation', 'mutated' or 'substitution', 'substituted' in this context mean that another amino acid is present on the indicated position than in the corresponding parent molecule, which here is a polypeptide comprising a FimH lectin domain with F at position 144. Such parent molecule may exist physically as polypeptide or in the form of nucleic acid encoding such polypeptide, but may also merely exist in silico or on paper as amino acid sequence or a corresponding nucleic acid sequence encoding the amino acid sequence. A mutation or substitution in this context is therefore also considered present for instance if a protein is expressed from a nucleic acid that has been synthesized such that it encodes the mutation or substitution, even though the nucleic acid encoding the corresponding parent molecule was not initially actually prepared during the process, e.g. when the nucleic acid molecule has been prepared entirely by chemical synthesis.

In one preferred embodiment, the polypeptide comprising the FimH lectin domain of the invention comprises the substitution of Phenylalanine (F) to Valine (V) at position 144. In certain embodiments, the polypeptide comprising the FimH lectin domain of the invention is a non-naturally occurring polypeptide which comprises a Valine at position 144. In certain embodiments, the polypeptide comprising the FimH lectin domain of the invention has a valine at position 144 instead of the naturally occurring phenylalanine.

In one embodiment, the FimH lectin domain has an amino acid sequence having at least about 90%, 91%, 92%, 93%, 94%, 95%, 96%, 97%, 98%, or 99% sequence identity with SEQ ID NO: 1. Preferably, the FimH lectin domain may comprise a sequence having SEQ ID NO: 1, with the exception of position 144 which for FimH lectin domain of the invention is substituted by valine (V), isoleucine (I), leucine (L), glycine (G), methionine (M), or alanine (A).

Full-length FimH (FimH$_{FL}$) is composed of two domains: the N-terminal lectin domain (FimH$_{LD}$) connected to the C-terminal pilin domain (FimH$_{PD}$) by a short tetra-peptides loop linker. In one embodiment of the invention, the polypeptide comprising the FimH lectin domain according to the invention further comprises a FimH pilin domain. In one preferred embodiment, the polypeptide of the invention is a full length FimH polypeptide wherein the FimH lectin domain comprises an amino acid selected from the group consisting of valine (V), isoleucine (I), leucine (L), glycine (G), methionine (M), and alanine (A) at the position that corresponds to position 144 in SEQ ID NO: 1.

In one embodiment, the polypeptide is a full length FimH having at least about 80%, 85%, 90%, 91%, 92%, 93%, 94%, 95%, 96%, 97%, 98%, or 99% sequence identity with SEQ ID NO: 2. Preferably, the full length FimH polypeptide may comprise a sequence having SEQ ID NO: 2, with the exception of the F144V substitution as described herein. In another embodiment, the polypeptide is a full length FimH having at least about 80%, 85%, 90%, 91%, 92%, 93%, 94%, 95%, 96%, 97%, 98%, or 99% sequence identity with SEQ ID NO: 4 or preferably at least with amino acids 22-300 thereof. Preferably, the full length FimH polypeptide may comprise a sequence having SEQ ID NO: 4 or more preferably at least amino acids 22-300 thereof, with the exception of the F144V substitution as described herein.

In certain embodiments, the polypeptide is a full length FimH having at least about 80%, 85%, 90%, 91%, 92%, 93%, 94%, 95%, 96%, 97%, 98%, or 99% sequence identity with SEQ ID NO: 23-45 and 55 as described in U.S. Pat. No. 6,737,063, which is incorporated herein in its entirety.

FimH polypeptides are not only highly conserved between various strains of E. coli, they are also highly conserved among a wide range of gram-negative bacteria. Moreover, the amino acid changes that occur between strains generally occur at similar amino acid positions. As a result of the high conservation of FimH between E. coli strains, FimH polypeptides from one strain are capable of inducing antibody responses that inhibit or prevent other E. coli strains from binding to cells by a FimH lectin and/or provide protection and/or treatment against infection caused by other E. coli strains. Accordingly, in one embodiment the full length FimH has at least about 80%, 85%, 90%, 95%, 96%, 97%, 98%, or 99% sequence identity with SEQ ID NO: 5, or preferably at least with amino acids 22-300 thereof. Preferably, the full length FimH polypeptide may comprise a sequence having SEQ ID NO: 5 or more preferably at least amino acids 22-300 thereof, with the exception of the F144V substitution as described herein. In another embodiment, the full length FimH has at least about 80%, 85%, 90%, 95%, 96%, 97%, 98%, or 99% sequence identity with SEQ ID NO: 6. Preferably, the full length FimH polypeptide may comprise a sequence having SEQ ID NO: 6, with the exception of the F144V substitution as described herein.

As used herein, the term "periplasmic chaperone" is defined as a protein localized in the periplasm of bacteria that is capable of forming complexes with a variety of chaperone-binding proteins via recognition of a common binding epitope (or epitopes). Chaperones serve as templates upon which proteins exported from the bacterial cell into the periplasm fold into their native conformations. Association of the chaperone-binding protein with the chaperone also serves to protect the binding proteins from degradation by proteases localized within the periplasm, increases their solubility in aqueous solution, and leads to their sequentially correct incorporation into an assembling pilus. Chaperone proteins are a class of proteins in gram-negative bacteria that are involved in the assembly of pili by mediating such assembly, but are not incorporated into the structure. FimC is the periplasmic chaperone protein of FimH. FimC has an amino acid sequence having at least 70%, 75%, 80%, 85%, 90%, 95%, 96%, 97%, 98%, 99% or about 100% sequence identity with SEQ ID NO: 3. In certain embodiments, FimC has an amino acid sequence having at least 70%, 75%, 80%, 85%, 90%, 95%, 96%, 97%, 98%, 99% or about 100% sequence identity with SEQ ID NO: 29 as described in U.S. Pat. No. 6,737,063, which is incorporated herein in its entirety. The non-covalent complex of FimC and FimH is named FimCH.

Accordingly, in a further aspect, the invention provides for a complex comprising a polypeptide comprising the FimH lectin domain according to the invention and further comprising a FimH pilin domain or a full length FimH as described herein and FimC.

In one embodiment of the invention, the polypeptide comprising a FimH lectin domain according to the invention further comprises a FimH pilin domain and is complexed with FimC to form a FimCH complex.

The inventors of the present application have created several FimH lectin domain variants with different amino acid changes and tested them for efficiency in various assays (see the examples). Surprisingly, not all the tested FimH proteins with lectin domain mutations were capable of being incorporated into a FimCH complex with the desired properties, i.e. having sufficient purity (protein concentration and degree of purity), integrity and functionality.

The herein described FimH lectin domain which comprises an amino acid selected from the group consisting of valine (V), isoleucine (I), leucine (L), glycine (G), methionine (M), and alanine (A), at the position that corresponds to position 144 in SEQ ID NO: 1 was capable of forming FimCH complex having the desired properties.

In one embodiment, the polypeptide comprising a FimH lectin domain according to the invention is a full length FimH having at least about 80%, 85%, 90%, 95%, 96%, 97%, 98%, or 99% sequence identity with SEQ ID NO: 2 and is complexed with FimC to form a FimCH complex. A full length FimH in its final form does typically not include the signal peptide, which is for instance shown as amino acids 1-21 of SEQ ID NOs: 4 and 5, i.e. a full-length FimH of SEQ ID NO: 4 or SEQ ID NO: 5 is understood to include amino acids 22-300 of these sequences while typically lacking amino acids 1-21 thereof. For recombinant production of a full length FimH it is useful to encode the FimH that includes the signal peptide in the recombinant host cell, to get transport across the inner (cytoplasmic) membrane via the general secretory pathway leading to periplasmic location of the polypeptide (sometimes referred to as 'periplasmic expression'), but in the final FimH polypeptide as isolated and for instance used in pharmaceutical compositions, the signal peptide typically is no longer present as a result of processing by the recombinant cell that is expressing the polypeptide.

In a more preferred embodiment, the FimCH complex comprises or consists of a FimC protein having at least 80%, 85%, 90%, 95%, 96%, 97%, 98%, 99% or at least about 100% sequence identity with SEQ ID NO: 3 and a FimH protein comprising a lectin domain having an amino acid selected from the group consisting of valine (V), isoleucine (I), leucine (L), glycine (G), methionine (M), and alanine (A), at the position that corresponds to position 144 in SEQ ID NO: 1. In an even more preferred embodiment, the FimCH complex comprises or consists of a FimC protein having at least 80%, 85%, 90%, 95%, 96%, 97%, 98%, 99% or at least about 100% sequence identity with SEQ ID NO: 3 and a FimH protein that comprises a F144V substitution in the lectin domain or a full-length FimH protein that comprises a F165V substitution (e.g. in SEQ ID NOs: 4 or 5 that still include the signal peptide). In a full length FimH that would still include the signal peptide amino acid position 165 corresponds to amino acid position 144 in the FimH lectin domain. The skilled person will know how to identify corresponding amino acid positions in full length FimH amino acid sequences and in FimH lectin domain amino acid sequences using amino acid sequence alignment algorithms as defined hereinabove.

In one embodiment, complexes comprising the *E. coli* chaperone FimC and a FimH lectin domain variant of the invention may be formed by co-expressing the FimH lectin domain variant polypeptide according to the invention along with FimC, from a recombinant cell.

In one embodiment, the FimCH complex comprises a FimC originating from one bacterial strain while FimH originates from a different bacterial strain. In another embodiment, the FimCH complex comprises a FimC and a FimH both originating from the same bacterial strain. In certain embodiments, FimH or FimC or both FimH and FimC may be artificial sequences not from actual bacterial isolates that exist in nature, e.g. they can also be based upon consensus sequences or combinations of natural isolates.

In one embodiment, the FimCH complex comprises at least one polypeptide that comprises a His-tag. In one embodiment, the full-length FimH according to the invention comprises a His-tag or the FimC as described herein comprises a His-tag. Preferably, in the FimCH complex, the FimC comprises the His-tag. A His-tag as used herein is a stretch of histidine (His) residues, e.g. six His residues, which may be added internally or preferably at the N- or C-terminus of a protein. Such a tag has well-known use for ease of purification.

In a further aspect, the invention pertains to a polynucleotide encoding a FimH polypeptide as defined herein above. The polynucleotide may be preceded by a promoter operably linked thereto. In certain embodiments, the promoter is endogenous to the FimH coding sequence. In certain embodiments, the promoter is an endogenous promoter driving the expression of FimH in a bacterium of the Enterobacteriaceae family. In other embodiments, the promoter is heterologous to the FimH coding sequence, e.g. a strong promoter known to the skilled person for use in recombinant expression systems is used. For example, a pET-DUET vector comprising an inducible Lac promoter can be used for FimH and/or FimC expression. In case of an inducible promotor, IPTG can be used to induce expression. Preferably, the polynucleotide is isolated from its natural environment. In certain embodiments, the invention provides an isolated polynucleotide according to the invention. The polypeptide can be a recombinant, synthetic or artificial polynucleotide. The polynucleotide may be in any form of nucleic acid, e.g. DNA or RNA, preferably DNA. The polynucleotide may comprise one or more nucleotides that are not present in a naturally occurring FimH encoding polynucleotide. Preferably, the polynucleotide has one or more nucleotides that are not present in a naturally occurring FimH-encoding polynucleotide at its 5'-end and/or 3'-end. The sequences of the encoded mature FimC and/or FimH may preferably be preceded by a signal peptide in the polypeptides as encoded by the respective polynucleotides, and the signal peptides may be endogenous signal peptides to the FimC and/or FimH polypeptides (i.e. signal peptides as occurring in nature for these proteins) respectively, or they may be heterologous signal peptides, i.e. signal peptides from other proteins or synthetic signal peptides. The signal peptides are useful for periplasmic expression, but are typically cleaved off and not present in the finally produced and purified FimC and/or FimH, respectively.

If required and/or if desired, the polypeptide comprising a FimH lectin domain according to the invention or the polynucleotide encoding the polypeptide comprising a FimH lectin domain according to the invention can be incorporated into a pharmaceutically active mixture by adding a pharmaceutically acceptable carrier.

Accordingly, in a further aspect, the invention also provides for a composition, preferably a pharmaceutical composition comprising a FimH lectin domain according to the invention or the polynucleotide encoding the polypeptide comprising a FimH lectin domain according to the invention.

The (pharmaceutical) compositions of the invention may comprise any pharmaceutically acceptable excipient including a carrier, filler, preservative, solubilizer and/or diluent. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's pharmaceutical sciences," XIII ed. Editor-in-Chief Eric W. Martin. Mack Publishing Co., Easton, Pa., 2013.

In certain embodiments, the compositions of the invention additionally comprise one or more buffers, e.g., Tris-buffered saline, phosphate buffer, and sucrose phosphate glutamate buffer.

In certain embodiments, the compositions of the invention additionally comprise one or more salts, e.g., Tris-hydrochloride, sodium chloride, calcium chloride, potassium chloride, sodium phosphate, monosodium glutamate, and aluminum salts (e.g., aluminum hydroxide, aluminum phosphate, potassium aluminum sulfate, or a mixture of such aluminum salts).

The compositions of the invention can be used for eliciting an immune response in a host to whom the composition is administered, i.e., are immunogenic. Thus, the compositions of the invention can be used as vaccines against an infection caused by a bacterium of the family of Enterobacteriaceae, preferably against an infection caused by Klebsiella, more preferably *E. coli* and can thus comprise any additional components suitable for use in a vaccine. For example, an additional component of a vaccine composition is an adjuvant as described herein.

In certain embodiments, the compositions of the invention additionally comprise a preservative, such as phenol, benzethonium chloride, 2-phenoxyethanol, or thimerosal. In a specific embodiment, the (pharmaceutical) compositions of the invention comprise 0.001% to 0.01% preservative. In other embodiments, the (pharmaceutical) compositions of the invention do not comprise a preservative.

In certain embodiments, the compositions of the invention are formulated to be suitable for the intended route of administration to a subject. For example, the compositions of the invention can be formulated to be suitable for subcutaneous, parenteral, oral, intradermal, transdermal, colorectal, intraperitoneal, intravaginal, or rectal administration. In a specific embodiment, the pharmaceutical composition can be formulated for intravenous, oral, buccal, intraperitoneal, intranasal, intratracheal, subcutaneous, intramuscular, topical, intradermal, transdermal or pulmonary administration, preferably intramuscular administration.

The compositions of the invention can be included in a container, pack, or dispenser together with instructions for administration.

In certain embodiments, the compositions of the invention can be stored before use, e.g., the compositions can be stored frozen (e.g., at about −20° C. or at about −70° C.); stored in refrigerated conditions (e.g., at about 2-8° C., e.g. about 4° C.); or stored at room temperature. Alternatively, separate compositions comprising one or more of the components (i), (ii), and (iii) may be stored and mixed to the vaccine combination composition comprising all three of (i), (ii) and (iii) prior to use. In yet another alternative, the separate compositions are provided in a combination administration schedule.

In one embodiment of the invention, the pharmaceutical composition of the invention can be administered together with a composition that comprises one or more polysaccharides covalently linked to a carrier protein. Preferably, such a composition comprises one or more bioconjugates of an *E. coli* O-antigen polysaccharide covalently linked to a carrier protein, such as for instance described in WO2019/175145 which is incorporated herein in its entirety.

In an embodiment, the pharmaceutical composition of the invention herein further comprises an adjuvant. As used herein, the term "adjuvant" refers to a compound that when administered in conjunction with or as part of a composition of the invention augments, enhances and/or boosts the immune response to FimH, but when the adjuvant compound is administered alone does not generate an immune response to the conjugate and/or FimH.

Adjuvants can enhance an immune response by several mechanisms including, e.g., lymphocyte recruitment, stimulation of B and/or T cells, and stimulation of antigen presenting cells.

Preferably, the pharmaceutical compositions of the invention comprise, or are administered in combination with, an adjuvant. The adjuvant for administration in combination with a composition of the invention can be administered before, concomitantly with, or after administration of the immunogenic compositions. In preferred embodiments, the FimH of the invention and the adjuvant are administered in the form of a single composition.

Specific examples of adjuvants include, but are not limited to, aluminum salts (alum) (such as aluminum hydroxide, aluminum phosphate, aluminum sulfate, and aluminum oxide, including nanoparticles comprising alum or nano-alum formulations), calcium phosphate (e.g. Masson J D et al, 2017, Expert Rev Vaccines 16: 289-299), monophosphoryl lipid A (MPL) or 3-de-O-acylated monophosphoryl lipid A (3D-MPL) (see e.g., United Kingdom Patent GB2220211, EP0971739, EP1194166, U.S. Pat. No. 6,491,919), AS01, AS02, AS03 and AS04 (all GlaxoSmithKline; see e.g. EP1126876, U.S. Pat. No. 7,357,936 for AS04, EP0671948, EP0761231, U.S. Pat. No. 5,750,110 for AS02), imidazopyridine compounds (see WO2007/109812), imidazoquinoxaline compounds (see WO2007/109813), delta-inulin (e.g. Petrovsky N and PD Cooper, 2015, Vaccine 33: 5920-5926), STING-activating synthetic cyclic-di-nucleotides (e.g. US20150056224), combinations of lecithin and carbomer homopolymers (e.g. U.S. Pat. No. 6,676,958), and saponins, such as Quil A and QS21 (see e.g. Zhu D and W Tuo, 2016, Nat Prod Chem Res 3: e113 (doi:10.4172/2329-6836.1000e113), optionally in combination with QS7 (see Kensil et al., in Vaccine Design: The Subunit and Adjuvant Approach (eds. Powell & Newman, Plenum Press, N Y, 1995); U.S. Pat. No. 5,057,540). In some embodiments, the adjuvant is Freund's adjuvant (complete or incomplete). In certain embodiments, the adjuvant comprises Quil-A, such as for instance commercially obtainable from Brenntag (now Croda) or Invivogen. QuilA contains the water-extractable fraction of saponins from the Quillaja *saponaria* Molina tree. These saponins belong to the group of triterpenoid saponins, that have a common triterpenoid backbone structure. Saponins are known to induce a strong adjuvant response to T-dependent as well as T-independent antigens, as well as strong cytotoxic CD8+ lymphocyte responses and potentiating the response to mucosal antigens. They can also be combined with cholesterol and phospholipids, to form immunostimulatory complexes (ISCOMs), wherein QuilA adjuvant can activate both antibody-mediated and cell-mediated immune responses to a broad range of antigens from different origens. In certain embodiments, the adjuvant is AS01, preferably AS01B. SO1 is an Adjuvant System containing MPL (3-O-desacyl-4'-monophosphoryl lipid A), QS21 (Quillaja *saponaria* Molina, fraction 21) and liposomes. In certain embodiments, the AS01 is commercially available (GSK) or can be made as described in WO 96/33739, incorporated herein by reference. Certain adjuvants comprise emulsions, which are mixtures of two immiscible fluids, e.g. oil and water, one of which is suspended as small drops inside the other, and are stabilized by surface-active agents. Oil-in-water emulsions have water forming the continuous phase, surrounding small droplets of oil, while water-in-oil emulsions have oil forming the continuous phase. Certain emulsions comprise squalene (a metabolizable oil). Certain adjuvants comprise block copolymers, which are copolymers formed when two monomers cluster together and form blocks of repeating units. An example of a water in oil emulsion comprising a block copolymer, squalene and a microparticulate stabilizer is TiterMax®, which can be commercially obtained from Sigma-Aldrich. Optionally emulsions can be combined with or comprise further immunostimulating components, such as a TLR4 agonist. Certain adjuvants are oil in water emulsions (such as squalene or peanut oil) also used in MF59 (see e.g. EP0399843, U.S. Pat. Nos. 6,299,884, 6,451,325) and AS03, optionally in combination with immune stimulants, such as monophosphoryl lipid A and/or QS21 such as in AS02 (see Stoute et al., 1997, N. Engl. J. Med. 336, 86-91). Further examples of adjuvants are liposomes containing immune stimulants such as MPL and QS21 such as in AS01E and AS01B (e.g. US 2011/0206758). Other examples of adjuvants are CpG (Bioworld Today, Nov. 15, 1998) and imidazoquinolines (such as imiquimod and R848). See, e.g., Reed G, et al., 2013, Nature Med, 19: 1597-1608.

In certain preferred embodiments, the adjuvant comprises saponins, preferably the water-extractable fraction of saponins obtained from Quillaja *saponaria*. In certain embodiments, the adjuvant comprises QS-21.

In certain preferred embodiments, the adjuvant contains a toll-like receptor 4 (TLR4) agonist. TLR4 agonists are well known in the art, see e.g. Ireton G C and SG Reed, 2013, Expert Rev Vaccines 12: 793-807. In certain preferred embodiments, the adjuvant is a TLR4 agonist comprising lipid A, or an analog or derivative thereof.

The adjuvant, preferably including a TLR4 agonist, may be formulated in various ways, e.g. in emulsions such as water-in-oil (w/o) emulsions or oil-in-water (o/w) emulsions (examples are MF59, AS03), stable (nano-)emulsions (SE), lipid suspensions, liposomes, (polymeric) nanoparticles, virosomes, alum adsorbed, aqueous formulations (AF), and the like, representing various delivery systems for immunomodulatory molecules in the adjuvant and/or for the immunogens (see e.g. Reed et al, 2013, supra; Alving C R et al, 2012, Curr Opin Immunol 24: 310-315).

The immunostimulatory TLR4 agonist may optionally be combined with other immunomodulatory components, such as saponins (e.g. QuilA, QS7, QS21, Matrix M, Iscoms, Iscomatrix, etc), aluminum salts, activators for other TLRs (e.g. imidazoquinolines, flagellin, CpG, dsRNA analogs, etc), and the like (see e.g. Reed et al, 2013, supra).

As used herein, the term "lipid A" refers to the hydrophobic lipid moiety of an LPS molecule that comprises glucosamine and is linked to keto-deoxyoctulosonate in the inner core of the LPS molecule through a ketosidic bond, which anchors the LPS molecule in the outer leaflet of the outer membrane of Gram-negative bacteria. For an overview of the synthesis of LPS and lipid A structures, see, e.g., Raetz, 1993, J. Bacteriology 175:5745-5753, Raetz C R and C Whitfield, 2002, Annu Rev Biochem 71: 635-700; U.S. Pat. Nos. 5,593,969 and 5,191,072. Lipid A, as used herein includes naturally occurring lipid A, mixtures, analogs, derivatives and precursors thereof. The term includes monosaccharides, e.g., the precursor of lipid A referred to as lipid X; disaccharide lipid A; hepta-acyl lipid A; hexa-acyl lipid A; penta-acyl lipid A; tetra-acyl lipid A, e.g., tetra-acyl precursor of lipid A, referred to as lipid IVA; dephosphorylated lipid A; monophosphoryl lipid A; diphosphoryl lipid A, such as lipid A from *Escherichia coli* and *Rhodobacter sphaeroides*. Several immune activating lipid A structures contain 6 acyl chains. Four primary acyl chains attached directly to the glucosamine sugars are 3-hydroxy acyl chains usually between 10 and 16 carbons in length. Two additional acyl chains are often attached to the 3-hydroxy groups of the primary acyl chains. *E. coli* lipid A, as an example, typically has four C14 3-hydroxy acyl chains attached to the sugars and one C12 and one C14 attached to the 3-hydroxy groups of the primary acyl chains at the 2' and 3' position, respectively.

Figure 1:
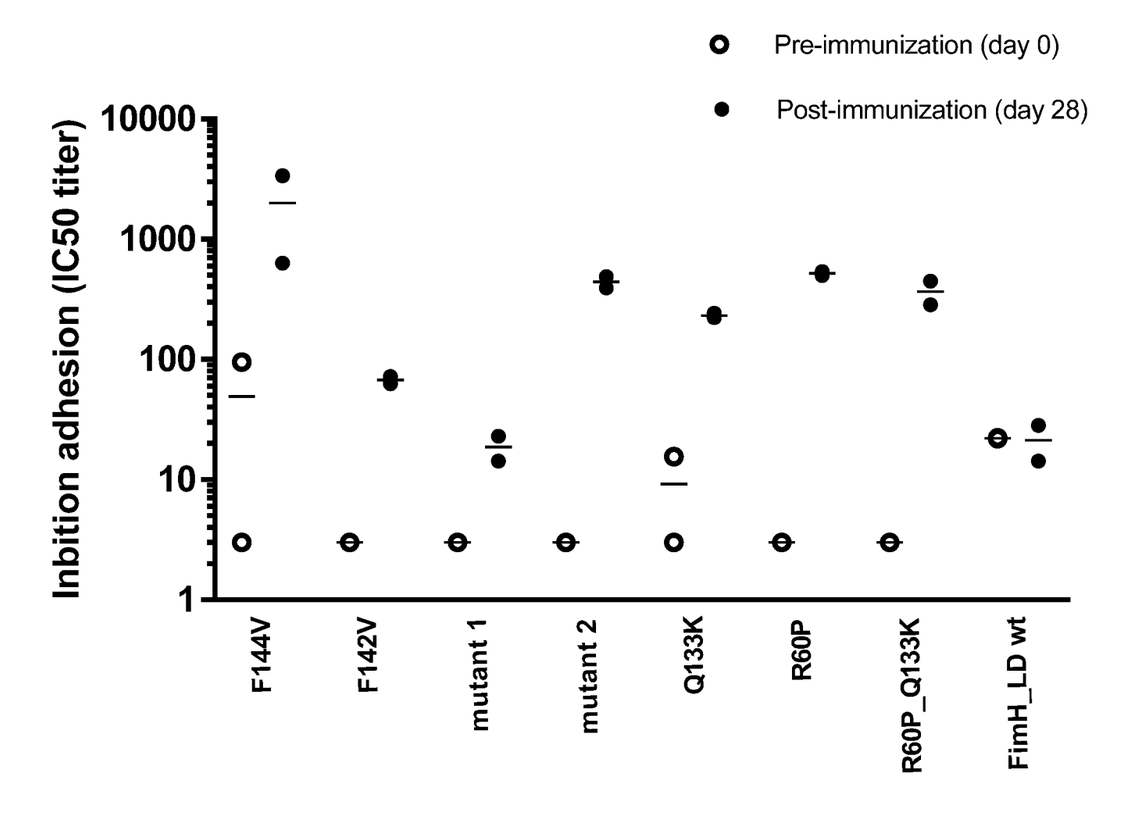

As used herein, the term "lipid A analog or derivative" refers to a molecule that resembles the structure and immunological activity of lipid A, but that does not necessarily naturally occur in nature. Lipid A analogs or derivatives may be modified to e.g. be shortened or condensed, and/or to have their glucosamine residues substituted with another amine sugar residue, e.g. galactosamine residues, to contain a 2-deoxy-2-aminogluconate in place of the glucosamine-1-phosphate at the reducing end, to bear a galacturonic acid moiety instead of a phosphate at position 4'. Lipid A analogs or derivatives may be prepared from lipid A isolated from a bacterium, e.g., by chemical derivation, or chemically synthesized, e.g. by first determining the structure of the preferred lipid A and synthesizing analogs or derivatives thereof. Lipid A analogs or derivatives are also useful as TLR4 agonist adjuvants (see, e.g. Gregg K A et al, 2017, MBio 8, eDD492-17, doi: 10.1128/mBio.00492-17). For example, a lipid A analog or derivative can be obtained by deacylation of a wild-type lipid A molecule, e.g., by alkali treatment. Lipid A analogs or derivatives can for instance be prepared from lipid A isolated from bacteria. Such molecules could also be chemically synthesized. Another example of lipid A analogs or derivatives are lipid A molecules isolated from bacterial cells harboring mutations in, or deletions or insertions of enzymes involved in lipid A biosynthesis and/or lipid A modification. MPL and 3D-MPL are lipid A analogs or derivatives that have been modified to attenuate lipid A toxicity. Lipid A, MPL and 3D-MPL have a sugar backbone onto which long fatty acid chains are attached, wherein the backbone contains two 6-carbon sugars in glycosidic linkage, and a phosphoryl moiety at the 4 position. Typically, five to eight long chain fatty acids (usually 12-14 carbon atoms) are attached to the sugar backbone. Due to derivation of natural sources, MPL or 3D-MPL may be present as a composite or mixture of a number of fatty acid substitution patterns, e.g. hepta-acyl, hexa-acyl, penta-acyl, etc., with varying fatty acid lengths. This is also true for some of the other lipid A analogs or derivatives described herein, however synthetic lipid A variants may also be defined and homogeneous. MPL and its manufacture are for instance described in U.S. Pat. No. 4,436,727. 3D-MPL is for instance described in U.S. Pat. No. 4,912,094B1, and differs from MPL by selective removal of the 3-hydroxymyristic acyl residue that is ester linked to the reducing-end glucosamine at position 3 (compare for instance the structure of MPL in column 1 vs 3D-MPL in column 6 of U.S. Pat. No. 4,912,094B1). In the art often 3D-MPL is used, while sometimes referred to as MPL (e.g. the first structure in Table 1 of Ireton G C and SG Reed, 2013, supra, refers to this structure as MPL®, but actually depicts the structure of 3D-MPL). Examples of lipid A (analogs, derivatives) according to the invention include MPL, 3D-MPL, RC529 (e.g. EP1385541), PET-lipid A, GLA (glycopyranosyl lipid adjuvant, a synthetic disaccharide glycolipid; e.g. US20100310602, U.S. Pat. No. 8,722,064), SLA (e.g. Carter D et al, 2016, Clin Transl Immunology 5: e108 (doi: 10.1038/cti.2016.63), which describes a structure-function approach to optimize TLR4 ligands for human vaccines), PHAD (phosphorylated hexaacyl disaccharide; the structure of which is the same as that of GLA), 3D-PHAD, 3D-(6-acyl)-PHAD (3D(6A)-PHAD) (PHAD, 3D-PHAD, and 3D(6A)PHAD are synthetic lipid A variants, see e.g. avantilipids.com/divisions/adjuvants, which also provide structures of these molecules), E6020 (CAS Number 287180-63-6), 0N04007, OM-174, and the like. For exemplary chemical structures of 3D-MPL, RC529, PET-lipid A, GLA/PHAD, E6020, ON04007, and OM-174, see e.g. Table 1 in Ireton G C and SG Reed, 2013, supra. For a structure of SLA, see e.g. FIG. 1 in Reed S G et al, 2016, Curr Opin Immunol 41: 85-90. In certain preferred embodiments, the TLR4 agonist adjuvant comprises a lipid A analog or derivative chosen from 3D-MPL, GLA, or SLA.

Exemplary adjuvants comprising a lipid A analog or derivative include GLA-LSQ (synthetic MPL [GLA], QS21, lipids formulated as liposomes), SLA-LSQ (synthetic MPL [SLA], QS21, lipids, formulated as liposomes), GLA-SE (synthetic MPL [GLA], squalene oil/water emulsion), SLA-SE (synthetic MPL [SLA], squalene oil/water emulsion), SLA-Nanoalum (synthetic MPL [SLA], aluminum salt), GLA-Nanoalum (synthetic MPL [GLA], aluminum salt), SLA-AF (synthetic MPL [SLA], aqueous suspension), GLA-AF (synthetic MPL [GLA], aqueous suspension,), SLA-alum (synthetic MPL [SLA], aluminum salt), GLA-alum (synthetic MPL [GLA], aluminum salt), and several of the GSK ASxx series of adjuvants, including AS01 (MPL, QS21, liposomes), AS02 (MPL, QS21, oil/water emulsion), AS25 (MPL, oil/water emulsion), AS04 (MPL, aluminum salt), and AS15 (MPL, QS21, CpG, liposomes). See, e.g., WO 2013/119856, WO 2006/116423, U.S. Pat. Nos. 4,987,237, 4,436,727, 4,877,611, 4,866,034, 4,912,094, 4,987,237, 5,191,072, 5,593,969, 6,759,241, 9,017,698, 9,149,521, 9,149,522, 9,415,097, 9,415,101, 9,504,743, Reed G, et al., 2013, supra, Johnson et al., 1999, J Med Chem, 42:4640-

4649, and Ulrich and Myers, 1995, Vaccine Design: The Subunit and Adjuvant Approach; Powell and Newman, Eds.; Plenum: New York, 495-524.

Non-glycolipid molecules may also be used as TLR4 agonist adjuvants, e.g. synthetic molecules such as Neoseptin-3 or natural molecules such as LeIF, see e.g. Reed S G et al, 2016, supra.

In another aspect the invention relates to a polypeptide comprising a FimH lectin domain of the invention, a polynucleotide of the invention or a pharmaceutical composition of the invention for use as a medicament.

In a further aspect the invention relates to the use of a polypeptide comprising a FimH lectin domain as described herein, a polynucleotide as described or a pharmaceutical composition described herein as a medicament for inducing an immune response against a gram negative bacterium of the family of Enterobacteriaceae.

As used herein the terms "immunogen" or "immunogenic" or "antigen" are used interchangeably to describe a molecule capable of inducing an immunological response against itself on administration to a recipient, either alone, in conjunction with an adjuvant, or presented on a display vehicle.

As used herein, an "immunological response" or "immune response" to an antigen or composition refers to the development in a subject of a humoral and/or a cellular immune response to the antigen or an antigen present in the composition.

In a further aspect, the invention relates to the polypeptide comprising a FimH lectin domain as described herein, a polynucleotide as described or a pharmaceutical composition described herein for use in inducing an immune response against a bacterial infection caused a gram negative bacterium of the family Enterobacteriaceae. In certain embodiments, the bacterial infection is caused by *Staphylococcus saprophyticus* or *Staphylococcus aureus*, *Proteus* spp., *Serratia* spp., or *Pseudomonas* spp. In preferred embodiments the bacterial infection is caused by *Klebsiella* spp., or *E. coli*. In a most preferred embodiment, the bacterial infection is caused by *E. coli*. Thus in one embodiment, the invention relates to the use of a polypeptide comprising a FimH lectin domain as described herein, a polynucleotide as described or a pharmaceutical composition described herein as a medicament for inducing an immune response against *E. coli* or *Klebsiella*, preferably *E. coli*.

In preferred embodiments, the bacterial infection, caused by a gram negative bacterium of the family Enterobacteriaceae is an infection by *E. coli*, e.g. by ExPEC, more particularly a urinary tract infection (UTI). In one embodiment, the invention relates to the polypeptide comprising a FimH lectin domain as described herein, a polynucleotide as described or a pharmaceutical composition described herein for use in treating, preventing, or suppressing symptoms and/or sequelae associated with a UTI in a subject. In certain embodiments, said UTI is a rUTI. *E. coli* is one of the main causative agents of UTIs and rUTIs which are an important health care problem in young females and older adults. Thus, in preferred embodiments, the bacterial infection is a UTI or rUTI caused by *E. coli*.

In one embodiment, the invention relates to a method of treating, preventing, or suppressing symptoms and/or sequelae associated with an enterobacillus-related condition a subject in need thereof. The method comprises administering to the subject an effective amount of the polypeptide comprising a FimH lectin domain as described herein, a polynucleotide as described or a pharmaceutical composition described herein. Preferably, the administration induces an immune response that is effective in treating or preventing an enterobacillus-related condition. Preferably, the enterobacillus-related condition is a urogenital tract infection, more particularly a UTI or rUTI.

The invention also relates to use of a polypeptide comprising a FimH lectin domain as described herein, a polynucleotide as described or a pharmaceutical composition described herein for the manufacture of a medicament for treating, preventing, or suppressing a bacterial infection caused a gram negative bacterium of the family Enterobacteriaceae, preferably a bacterial infection caused by *E. coli*. More preferably, the bacterial infection is a UTI or rUTI caused by *E. coli*.

In a further aspect, the invention relates to vector comprising a polynucleotide encoding a polypeptide of the invention. In certain embodiments, the vector is a plasmid or a viral vector, preferably a plasmid. The vector is preferably in the form of DNA, e.g. a DNA plasmid. In certain embodiments, the vector comprises the polynucleotide of the invention operably linked to a promoter, meaning that the polynucleotide is under control of a promoter. The promoter may be located upstream of the polynucleotide that encodes the polypeptide of the invention, e.g. in an expression cassette in a plasmid.

The invention further relates to a method for the production of a polypeptide of the invention, the method comprising culturing a recombinant cell containing the polynucleotide encoding the polypeptide comprising a FimH lectin domain as described herein and/or the vector as described herein, wherein the culturing takes place under conditions conducive to the production of the polypeptide. In certain embodiments, the method further comprises recovering the polypeptide, which is optionally followed by formulation into a pharmaceutical composition.

Preferably an *E. coli* cell, for example an *E. coli* BL21 derivative, cell is used in the method for producing the polypeptide comprising a FimH lectin domain according to the invention.

The recovery of the polypeptide preferably includes a purification and/or isolation step which can be performed using conventional protein purification methods well known in the art. Such methods may include ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography.

Typical examples for such purification and/or isolation may utilize an antibody to the protein or to a His tag or cleavable leader or tail that is expressing as part of the protein structure. In certain embodiments, the polypeptide described herein have a His-tag included and are purified by methods such as IMAC affinity purification. In certain embodiments, the polypeptides described herein do not comprise a His-tag, in such cases purification is performed by cation exchange chromatography (cIEX) and hydrophobic interaction chromatography (HIC).

Definitions

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning commonly understood to one of ordinary skill in the art to which this invention pertains. Otherwise, certain terms cited herein have the meanings as set in the specification. All patents, published patent applications and publications cited herein are incorporated by reference as if set forth fully herein. It must be noted that as used herein and in the appended claims, the singular forms "a," "an," and "the" include plural reference unless the context clearly dictates otherwise.

Throughout this description and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. Any of the aforementioned terms of "comprising", "containing", "including", and "having", whenever used herein in the context of an aspect or embodiment of the invention can be replaced with the term "consisting of" or "consisting essentially of" to vary scopes of the disclosure.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, the term "pharmaceutically acceptable carrier" refers to a non-toxic material that does not interfere with the effectiveness of a composition according to the invention or the biological activity of a composition according to the invention. A "pharmaceutically acceptable carrier" can include any excipient, diluent, filler, salt, buffer, stabilizer, solubilizer, oil, lipid, lipid containing vesicle, microsphere, liposomal encapsulation, or other material well known in the art for use in pharmaceutical formulations. It will be understood that the characteristics of the pharmaceutically acceptable carrier will depend on the route of administration for a particular application. According to particular embodiments, in view of the present disclosure, any pharmaceutically acceptable carrier suitable for use in a vaccine can be used in the invention. Suitable excipients include but are not limited to sterile water, saline, dextrose, glycerol, ethanol, or the like and combinations thereof, as well as stabilizers, e.g. Human Serum Albumin (HSA) or other suitable proteins and reducing sugars.

As used herein, the term "effective amount" refers to an amount of an active ingredient or component that elicits the desired biological or medicinal response in a subject. An effective amount can be determined empirically and in a routine manner, in relation to the stated purpose. For example, in vitro assays can optionally be employed to help identify optimal dosage ranges.

As used herein, "subject" or "patient" means any animal, preferably a mammal, most preferably a human, who will be or has been vaccinated by a method or composition according to an embodiment of the invention. The term "mammal" as used herein, encompasses any mammal. Examples of mammals include, but are not limited to, cows, horses, sheep, pigs, cats, dogs, mice, rats, rabbits, guinea pigs, monkeys, humans, etc., most preferably a human. In certain embodiments, a subject is a human adult. As used herein, the term "human adult" refers to a human that is 18 years or older. In certain embodiments, a subject is less than 18 years old, e.g. 0-18 years old, e.g. 9-18 years old, or 12-18 years old. In certain embodiments, a subject is a human subject of about 18 to about 50 years. In certain embodiments, a subject is a human of about 50 to about 100 years, e.g. 50-85 years, 60-80 years, 50 years or older, 55 years or older, 60 years or older, 65 years or older, 70 years or older, 75 years or older, 80 years or older, 85 years or older. In some embodiments hereof the subject is not older than 85 years, not older than 80 years, not older than 75 years. In certain embodiments, a human subject is a male. In certain embodiments, a human subject is a female.

As used herein, a "UTI" means an infection of the kidney, bladder, ureter, or urethra. Symptoms of UTI may include one or more of burning feeling when urinating, frequent or intense urge to urinate, incomplete bladder emptying, urine having abnormal look and/or smell, elevated white blood cells in urine, feeling tired or shaky, feeling disoriented, fever or chills, malaise, pain or pressure in back, lower abdomen, pelvis or bladder. However, in some patients, symptoms may be absent or non-specific. Sequelae of UTI may include systemic complications such as invasive disease and sepsis. In certain embodiments, a UTI is clinically and/or microbiologically documented, e.g. confirmed with bacterial culture of urine and/or with molecular or other methods. In certain embodiments, the subject is a human subject that previously has had or currently is having a UTI. In certain embodiments, the subject has had a UTI within the last two years, the last year, or the last 6 months. In certain embodiments, the subject has had or currently has a recurrent UTI (rUTI). A "rUTI" as used herein means at least two infections in six months or at least three UTIs in one year. In certain embodiments, a subject to which the polypeptide comprising a FimH lectin domain of the invention, the FimCH complex of the invention, or a composition of the invention is administered, has suffered at least two UTIs within the last two years, within the last year, or within the last six months. In certain embodiments, the subject has suffered from complicated UTI. A 'complicated UTI' as used herein means a UTI associated with a condition, such as structural or functional abnormalities of the genitourinary tract or the presence of an underlying disease. In certain embodiments, a UTI leads to elevated numbers of white blood cells in urine or other urine abnormalities. In certain embodiments, a subject with UTI has a number of bacteria in urine, i.e. the urine is not sterile, e.g. a bacterial cell count of at least about 10 cells/mL, at least about 100 cells/mL, at least about $10^3$ cells/mL, e.g. at least about $10^4$ cells/mL, e.g. at least about $10^5$ cells/mL.

As used herein, an "immunological response" or "immune response" to an antigen or composition refers to the development in a subject of a humoral and/or a cellular immune response to the antigen or an antigen present in the composition.

Unless otherwise indicated, the term "at least" preceding a series of elements is to be understood to refer to every element in the series.

The word "about" or "approximately" when used in association with a numerical value (e.g. about 10) preferably means that the value may be the given value (of 10) more or less 10%, preferably more or less 5% of the value.

The terms "homology", "sequence identity" and the like are used interchangeably herein. Sequence identity is herein defined as a relationship between two or more amino acid (polypeptide or protein) sequences or two or more nucleic acid (polynucleotide) sequences, as determined by comparing the sequences. In the art, "identity" also means the degree of sequence relatedness between amino acid or nucleic acid sequences, as the case may be, as determined by the match between strings of such sequences. "Similarity" between two amino acid sequences is determined by comparing the amino acid sequence and its conserved amino acid substitutes of one polypeptide to the sequence of a second polypeptide. "Identity" and "similarity" can be readily calculated by known methods.

"Sequence identity" and "sequence similarity" can be determined by alignment of two peptide or two nucleotide sequences using global or local alignment algorithms, depending on the length of the two sequences. Sequences of similar lengths are preferably aligned using a global alignment algorithm (e.g. Needleman Wunsch) which aligns the sequences optimally over the entire length, while sequences of substantially different lengths are preferably aligned using a local alignment algorithm (e.g. Smith Waterman). Sequences may then be referred to as "substantially identical" or "essentially similar" when they (when optimally aligned by for example the programs GAP or BESTFIT using default parameters) share at least a certain minimal percentage of sequence identity (as defined below). GAP uses the Needleman and Wunsch global alignment algorithm to align two sequences over their entire length (full length), maximizing the number of matches and minimizing the number of gaps. A global alignment is suitably used to determine sequence identity when the two sequences have similar lengths. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA, or using open source software, such as the program "needle" (using the global Needleman Wunsch algorithm) or "water" (using the local Smith Waterman algorithm) in EmbossWIN version 2.10.0, using the same parameters as for GAP above, or using the default settings (both for 'needle' and for 'water' and both for protein and for DNA alignments, the default Gap opening penalty is 10.0 and the default gap extension penalty is 0.5; default scoring matrices are Blosum62 for proteins and DNAFull for DNA). When sequences have a substantially different overall lengths, local alignments, such as those using the Smith Waterman algorithm, are preferred.

Alternatively, percentage similarity or identity may be determined by searching against public databases, using algorithms such as FASTA, BLAST, etc. Thus, the nucleic acid and protein sequences of the present invention can further be used as a "query sequence" to perform a search against public databases to, for example, identify other family members or related sequences. Such searches can be performed using the BLASTn and BLASTx programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to nucleic acid molecules of the invention. BLAST protein searches can be performed with the BLASTx program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., BLASTx and BLASTn) can be used. See the homepage of the National Center for Biotechnology Information at hypertext://www.ncbi.nlm.nih.gov/.

DESCRIPTION OF THE SEQUENCES

TABLE 1

Sequences

| Description | SEQUENCE | SEQ ID NO. |
|---|---|---|
| FimH$_{LD}$ sequence (FimH$_{LD}$ 23-10) | FACKTANGTAIPIGGGSANVYVNLAPAVNVGQNLVVDLSTQIF CHNDYPETITDYVTLQRGSAYGGVLSNFSGTVKYSGSSYPFPT TSETPRVVYNSRTDKPWPVALYLTPVSSAGGVAIKAGSLIAVL ILRQTNNYNSDDFQFVWNIYANNDVVVPTG | 1 |
| FimHt sequence | FACKTANGTAIPIGGGSANVYVNLAPAVNVGQNLVVDLSTQIF CHNDYPETITDYVTLQRGSAYGGVLSNFSGTVKYSGSSYPFPT TSETPRVVYNSRTDKPWPVALYLTPVSSAGGVAIKAGSLIAVL ILRQTNNYNSDDFQFVWNIYANNDVVVPTGGCDVSARDVTVTL PDYPGSVPIPLTVYCAKSQNLGYYLSGTTADAGNSIFTNTASF SPAQGVGVQLTRNGTIIPANNTVSLGAVGTSAVSLGLTANYAR TGGQVTAGNVQSIIGVTFVYQ | 2 |
| FimC full length | GVALGATRVIYPAGQKQVQLAVTNNDENSTYLIQSWVENADGV KDGRFIVTPPLFAMKGKKENTLRILDATNNQLPQDRESLFWMN VKAIPSMDKSKLTENTLQLAIISRIKLYYRPAKLALPPDQAAE KLRFRRSANSLTLINPTPYYLTVTELNAGARVLENALVPPMGE STVKLPSDAGSNITYRTINDYGALTPKMTGVME | 3 |

TABLE 1-continued

Sequences

| Description | SEQUENCE | SEQ ID NO. |
|---|---|---|
| Example of FimH 23-10 (full length) sequence | MKRVITLFAVLLMGWSVNAWSFACKTANGTAIPIGGGSANVYV NLAPAVNVGQNLVVDLSTQIFCHNDYPETITDYVTLQRGSAYG GVLSNFSGTVKYSGSSYPFPTTSETPRVVYNSRTDKPWPVALY LTPVSSAGGVAIKAGSLIAVLILRQTNNYNSDDFQFVWNIYAN NDVVVPTGGCDVSARDVTVTLPDYPGSVPIPLTVYCAKSQNLG YYLSGTTADAGNSIFTNTASFSPAQGVGVQLTRNGTIIPANNT VSLGAVGTSAVSLGLTANYARTGGQVTAGNVQSIIGVTFVYQ | 4 |
| SEQ ID NO: 2 of U.S. Pat. No. 6,500,434 (example full length FimH sequence) | MKRVITLFAVLLMGWSVNAWSFACKTANGTAIPIGGGSANVYV NLAPVVNVGQNLVVDLSTQIFCHNDYPETITDYVTLQRGSAYG GVLSNFSGTVKYSGSSYPFPTTSETPRVVYNSRTDKPWPVALY LTPVSSAGGVAIKAGSLIAVLILRQTNNYNSDDFQFVWNIYAN NDVVVPTGGCDVSARDVTVTLPDYRGSVPIPLTVYCAKSQNLG YYLSGTHADAGNSIFTNTASFSPAQGVGVQLTRNGTIIPANNT VSLGAVGTSAVSLGLTANYARTGGQVTAGNVQSIIGVTFVTQ | 5 |
| SEQ ID NO: 29 of U.S. Pat. No. 6,737,063 (example FimH sequence with truncation at N-terminus) | FACKTANGTAIPIGGGSANVYVNLAPVVNVGQNLVVDLSTQIF CHNDYPETITDYVTLQRGSAYGGVLSNFSGTVKYSGSSYPFPT TSETPRVVYNSRTDKPWPVALYLTPVSSAGGLVIKAGSLIAVL ILRQTNNYNSDDFQFVWNIYANNDVVVPTGGCDVSARDVTVTL PDYRGSVPIPLTVYCAKSQNLGYYLSGTHADAGNSIFTNTASF SPAQGVGVQLTRNGTIIPTNNTVSLGAVGTSAVSLGLTANYAR TGGQVTAGNVQSIIGVTFVYQ | 6 |
| Example of a FimH$_{LD}$ sequence | FACKTANGTAIPIGGGSANVYVNLAPVVNVGQNLVVDLSTQIF CHNDYPETITDYVTLQRGSAYGGVLSNFSGTVKYSGSSYPFPT TSETPRVVYNSRTDKPWPVALYLTPVSSAGGLVIKAGSLIAVL ILRQTNNYNSDDFQFVWNIYANNDVVVPTGG | 7 |

Other examples of sequences for FimH polypeptides are described in U.S. Pat. No. 6,737,063, for example any one of SEQ ID NO: 23-45 or 55 therein, and these are all incorporated by reference herein.

EXAMPLES

The following examples of the invention are to further illustrate the nature of the invention. It should be understood that the following examples do not limit the invention and that the scope of the invention is to be determined by the appended claims.

Example 1: Design Novel Variants—SPR Data

To understand the impact of FimH conformational changes in the vaccine efficacy, several variants of FimH that contain different mutations that could potentially lock the protein in the low affinity status were designed, aiming to identify the best FimH variant that induce functional antibodies capable of reducing bacterial adhesion and colonization of the bladder.

Materials and Methods

FimH Design and Expression

FimC and FimH were expressed in a pET-DUET vector using heterologous signal sequences for expression in the periplasm and a C-terminal His-tag on FimC for affinity purification using immobilized metal affinity chromatography (IMAC). Expression was induced using IPTG and protein was extracted and purified using IMAC purification (Talon).

SPR

To gain a detailed insight into the binding affinity and kinetics of the interaction of FimH lectin domain variants with the nheptyl-α-D-mannopyranoside ligand, surface plasmon resonance (SPR) measurements were performed. In brief, all FimH variants were titrated into the Mannoside ligand 5 surface (Rabbani S et al, J Biol. Chem., 2018, 293(5):1835-1849) with the top concentrations of either 3 or 10 µM in the HBS-N (0.01 M HEPES, pH 7.4, 0.15 M NaCl, 3 mM EDTA, 0.05% surfactant P20). The proteins were injected from 0.12 to 10 µM or 0.036 to 3.0 µM using a single cycle kinetics injection.

Results

Several FimH variants were designed with the goal of finding a FimH lectin domain variant that could induce functional inhibitory antibodies, thereby preventing bacterial binding to bladder cells while providing broad coverage. To optimize the chances of finding a suitable FimH lectin domain variant, variants with a different predicted mode of action were selected.

Previously described mutants FimH_Q133K and FimH_R60P have a mutation in the mannose interacting residues in the binding pocket. These mutations are predicted to directly influence the binding interaction with mannose. These mutants were taken as positive controls. The double mutant R60P_Q133K was taken along to check for potentially enhanced effects. Additionally, wild-type (WT) FimH lectin domain was taken along as a negative control. Several further FimH mutants (including the ones referred to as 'Mutant 1' and 'Mutant 2' herein) were created and tested as candidates in the panel with the aim of obtaining functional inhibitory antibodies.

First the variants affinity for binding to mannose was assessed using SPR. The results are presented in table 2. As expected, the lectin domain variants having mutations in the mannose binding pocket of FimH (Q133K and R60P_Q133K) did not bind to mannoside at all. The R60P mutant showed low affinity for mannoside, as expected.

F142V still showed some affinity for mannoside, indicating that this mutation did not completely abolish binding to mannoside. In the FimH lectin domain variants comprising the F144V substitution the binding to mannoside was completely abolished. It was surprising to see that there was a difference between F142V and F144V in binding to mannoside given the very close proximity of the positions in the amino acid sequence as compared to the F144V mutation.

TABLE 2

Affinity measurements of FimH-LD variants to mannoside

| Variant | Affinity* |
|---|---|
| F144V | No binding |
| F142V | Medium affinity |
| Mutant 1 | Medium affinity |
| Mutant 2 | Low affinity |
| R60P | Low affinity |
| R60P-Q133K | No binding |
| Q133K | No binding |
| FimH LD wt | High affinity |

*Low affinity KD > 1000 nm; Medium affinity KD 100-1000 nM; High affinity KD < 100 nM

Example 2: Ability to Induce Inhibiting Antibodies

It has been shown that antibodies generated against FimH in the low affinity conformation are capable of blocking the bacterial cell and reducing colony formation in the bladder. To evaluate the functionality of antibodies induced by the different variants of FimH locked in the low affinity conformation an adhesion inhibition assay (AIA) was used.

Materials and Methods

Immunization Wistar rats received 4 intramuscular (i.m.) immunizations at day 0, 7, 10 and 18 with the hereinabove described FimH variants (60 μg each variant/dose) combined with a non-Freund adjuvant (Speedy rat 28-Day model, Eurogentec). Functionality of serum antibodies was investigated at day 0 (pre-immunization) and day 28 (post-immunization) by Adhesion Inhibition Assay (AIA) as described below.

Adhesion Inhibition Assay (AIA)

Bacteria (*E. coli* J96) were labeled with a fluorescein isothiocyanate (FITC). Labeled bacteria were incubated with bladder urothelial cells (5637 cell line) for 1 h at 37° C. The % of adherent bacteria was measured by flow cytometry. For evaluation of serum inhibition, bacteria are previously incubated with serum samples for 30 minutes at 37° C. and then mixed with 5637 cells.

ELISA 96-well plates are coated overnight with 1 ug/mL of FimH. After washing, coated wells are incubated with blocking buffer [phosphate-buffered saline (PBS)+2% bovine serum albumin (BSA)] for 1 hour at room temperature. After washing with PBS+0.05% TWEEN 20, serum is added to the plates that are then incubated for 1 hour at room temperature. After washing, goat anti-rat antibody conjugated to horseradish peroxidase diluted in PBS with 2% BSA is added to each well for 1 hour at room temperature. After a final washing, the reaction is developed with tetramethylbenzidine substrate. The reaction is stopped with 1M phosphoric acid, and absorbance is measured at 450 nm.

Results

Serum antibody inhibitory titers were calculated as half maximal inhibitory concentration (IC50) based on a 4-parameter logistic regression model. In addition, levels of serum antibodies induced by different FimH variants (total IgG) were evaluated by ELISA. EC50 titers, defined as half maximal effective concentration, were calculated based on duplicate 12-step titration curves that were analyzed with a 4PL nonlinear regression model. Evaluation of the magnitude of inhibitory antibodies induced by each of the FimH variants showed that, FimH-23-10_F144V was capable of inducing the highest levels of functional antibodies (FIG. 1), which was surprising and entirely unpredictable prior to the present invention. Based on this result the FimH lectin domain comprising the F144V substitution was selected as the lead candidate.

Example 3: Functionality of Antibodies

Functionality of antibodies was evaluated in biolayer interferometry analysis (Octet, Pall Fortebio) using purified IgG preparations to assess whether inhibitory antibodies were present. Briefly, 4 different concentrations of purified IgG (between 0-125 microgram/ml) were mixed with a FimH variant as described herein. After mixing, the FimH lectin domain protein was assessed for capability of binding to a biosensor which was pre-immobilized with biotin-labeled monomannoside (using biotin streptavidin chemistry). Association and dissociation was measured for 600 seconds and the response (in nanometer (nm)) during association was calculated and compared. This was done with mannoside compared to blank controls to assess the FimH variants capability of inhibiting binding of FimH to mannose.

Results

Changes in the FimH binding pocket conformation (resulting in low- medium- or high affinity binding of FimH to mannosides) play an important role in bacterial binding to uroepithelial cells. It has been suggested that antibodies against the conformation having low-affinity for mannose would have an inhibitory effect to bacterial adhesion. To analyze this suggestion and to further understand the impact of FimH conformational changes on vaccine efficacy, purified IgG from sera of rats immunized with the FimH lectin domain variants were screened for ability to reduce binding of FimH to a simple mannoside (monomannose-biotin) by biolayer interferometry (BLI).

The BLI-screen for presence of inhibiting antibodies in sera from rats immunized with FimH lectin domain variants showed that FimH-23-10_F144V was capable of inhibiting binding of both low- and high affinity FimH lectin domain proteins to immobilized mono-mannoside (data not shown).

Example 4: Ability to Bind Characterized Inhibitory mAbs 475 and 926

Mutations in the lectin domain of FimH may cause the loss of epitopes that are crucial in eliciting a strong and functional immune response such as the epitopes that are present in the binding pocket of FimH. To ensure that the integrity of the binding pocket was not compromised in the mutations described herein, the binding of monoclonal antibodies (mAb) mAb475 and mAb926 to the mutant FimH lectin domains was assessed. mAb475 and mAb926, recognize overlapping but distinct epitopes on the FimH lectin domain within the mannose-binding pocket of the FimH (Kisiela et al. 2013 & 2015).

Results

Mutated FimH lectin domains have been previously described in WO02102974. WO02102974 describes an extensive list of possible mutations of mostly unspecified mutations (65 possible mutation sites are suggested in the lectin domain of FimH which is approximately 159 amino acids long). However, WO02102974 indicates that the FimH lectin domains having an amino acid substitution at position 54, 133 or 135 are the most promising candidates, FimH_Q133K is explicitly mentioned as a highly preferred option. It was therefore quite surprising that FimH-23-10_Q133K was not recognized by the functional mAb475, indicating integrity issues of the binding pocket (Table 3). In contrast, FimH-23-10_F144V was recognized by both mAb475 and mAb926 indicating that the binding pocket remained completely intact (Table 3).

TABLE 3

Ability to bind characterized inhibitory mAbs 475 and 926

| Variant | Binding pocket integrity mAb 475 | mAb 926 |
| --- | --- | --- |
| F144V | Binding | Binding |
| R60P | Binding | Binding |
| R60P-Q133K | No binding | Binding |
| Q133K | No binding | Binding |
| FimH_LD wt | Binding | Binding |

Thus, in conclusion, of all of the FimH variants, FimH_F144V showed strongly reduced affinity for mannose (indicating that the variant was in the low affinity for mannose conformation) and was capable of inhibiting binding of both low- and high affinity FimH lectin domain proteins to immobilized mono-mannoside. Furthermore, FimH_F144V induced the highest levels of functional antibodies out of all the mutations tested and was shown to have an intact binding pocket. This mutant was also manufacturable in a FimCH complex. In conclusion, FimH lectin domain with a valine at position 144 has a surprising combination of features that make it very suitable as a vaccine component, i.e. better than wild-type on which efforts to develop a FimH-based vaccine have hitherto appear to have been focused, and better than the other variants tested herein.

The invention claimed is:

1. An isolated polynucleotide encoding a polypeptide comprising a FimH lectin domain, wherein the FimH lectin domain comprises an amino acid selected from the group consisting of valine (V), isoleucine (I), leucine (L), glycine (G), and methionine (M), at the position that corresponds to position 144 in SEQ ID NO: 1 wherein the FimH lectin domain has an amino acid sequence having at least 90% sequence identity with SEQ ID NO: 1.

2. The isolated polynucleotide of claim 1, wherein the polynucleotide encodes a polypeptide comprising a mutation and wherein the mutation is a F144V substitution.

3. The isolated polynucleotide of claim 1, wherein the FimH lectin domain has an amino acid sequence having at least 95% sequence identity with SEQ ID NO: 1.

4. The isolated polynucleotide of claim 1, wherein the polynucleotide further encodes a FimH pillin domain.

5. The isolated polynucleotide of claim 1, wherein the polynucleotide encodes a full length FimH having at least 90% sequence identity with SEQ ID NO: 2.

6. A vector comprising the isolated polynucleotide according to claim 1 operably linked to a promotor.

7. A method of producing a polypeptide comprising a FimH lectin domain, wherein the FimH lectin domain comprises an amino acid selected from the group consisting of valine (V), isoleucine (I), leucine (L), glycine (G), and methionine (M), at the position that corresponds to position 144 in SEQ ID NO: 1, wherein the FimH lectin domain has an amino acid sequence having at least 90% sequence identity with SEQ ID NO: 1, the method comprising expressing the polypeptide from a recombinant cell containing the vector of claim 6.

8. The method of claim 7, wherein the method further comprises recovering and purifying the polypeptide.

9. The method of claim 8, wherein the recovered and purified polypeptide is formulated into a pharmaceutical composition.

10. The isolated polynucleotide of claim 2, wherein the FimH lectin domain has an amino acid sequence having at least 95% sequence identity with SEQ ID NO: 1.

11. The isolated polynucleotide of claim 10, wherein the FimH lectin domain has an amino acid sequence having at least 97% sequence identity with SEQ ID NO: 1.

12. The isolated polynucleotide of claim 11, wherein the FimH lectin domain has an amino acid sequence comprising SEQ ID NO: 1 with a valine (V) at the position that corresponds to position 144 in SEQ ID NO: 1.

13. A vector comprising the isolated polynucleotide of claim 10, wherein the polypeptide is operably linked to a promotor.

14. A vector comprising the isolated polynucleotide of claim 11, wherein the polypeptide is operably linked to a promotor.

15. A vector comprising the isolated polynucleotide of claim 12, wherein the polypeptide is operably linked to a promotor.

* * * * *

SEQUENCE LISTING

```
Sequence total quantity: 7
SEQ ID NO: 1              moltype = AA  length = 159
FEATURE                   Location/Qualifiers
source                    1..159
                          mol_type = protein
                          organism = synthetic construct
SEQUENCE: 1
FACKTANGTA IPIGGGSANV YVNLAPAVNV GQNLVVDLST QIFCHNDYPE TITDYVTLQR   60
GSAYGGVLSN FSGTVKYSGS SYPFPTTSET PRVVYNSRTD KPWPVALYLT PVSSAGGVAI  120
KAGSLIAVLI LRQTNNYNSD DFQFVWNIYA NNDVVVPTG                        159

SEQ ID NO: 2              moltype = AA  length = 279
FEATURE                   Location/Qualifiers
source                    1..279
                          mol_type = protein
                          organism = synthetic construct
SEQUENCE: 2
FACKTANGTA IPIGGGSANV YVNLAPAVNV GQNLVVDLST QIFCHNDYPE TITDYVTLQR   60
GSAYGGVLSN FSGTVKYSGS SYPFPTTSET PRVVYNSRTD KPWPVALYLT PVSSAGGVAI  120
KAGSLIAVLI LRQTNNYNSD DFQFVWNIYA NNDVVVPTGG CDVSARDVTV TLPDYPGSVP  180
IPLTVYCAKS QNLGYYLSGT TADAGNSIFT NTASFSPAQG VGVQLTRNGT IIPANNTVSL  240
GAVGTSAVSL GLTANYARTG GQVTAGNVQS IIGVTFVYQ                        279

SEQ ID NO: 3              moltype = AA  length = 205
FEATURE                   Location/Qualifiers
source                    1..205
                          mol_type = protein
                          organism = synthetic construct
SEQUENCE: 3
GVALGATRVI YPAGQKQVQL AVTNNDENST YLIQSWVENA DGVKDGRFIV TPPLFAMKGK   60
KENTLRILDA TNNQLPQDRE SLFWMNVKAI PSMDKSKLTE NTLQLAIISR IKLYYRPAKL  120
ALPPDQAAEK LRFRRSANSL TLINPTPYYL TVTELNAGAR VLENALVPPM GESTVKLPSD  180
AGSNITYRTI NDYGALTPKM TGVME                                       205

SEQ ID NO: 4              moltype = AA  length = 300
FEATURE                   Location/Qualifiers
source                    1..300
                          mol_type = protein
                          organism = synthetic construct
SEQUENCE: 4
MKRVITLFAV LLMGWSVNAW SFACKTANGT AIPIGGGSAN VYVNLAPAVN VGQNLVVDLS   60
TQIFCHNDYP ETITDYVTLQ RGSAYGGVLS NFSGTVKYSG SSYPFPTTSE TPRVVYNSRT  120
DKPWPVALYL TPVSSAGGVA IKAGSLIAVL ILRQTNNYNS DDFQFVWNIY ANNDVVVPTG  180
```

```
                                            -continued
GCDVSARDVT VTLPDYPGSV PIPLTVYCAK SQNLGYYLSG TTADAGNSIF TNTASFSPAQ     240
GVGVQLTRNG TIIPANNTVS LGAVGTSAVS LGLTANYART GGQVTAGNVQ SIIGVTFVYQ     300

SEQ ID NO: 5            moltype = AA  length = 300
FEATURE                 Location/Qualifiers
source                  1..300
                        mol_type = protein
                        organism = synthetic construct
SEQUENCE: 5
MKRVITLFAV LLMGWSVNAW SFACKTANGT AIPIGGGSAN VYVNLAPVVN VGQNLVVDLS      60
TQIFCHNDYP ETITDYVTLQ RGSAYGGVLS NFSGTVKYSG SSYPFPTTSE TPRVVYNSRT     120
DKPWPVALYL TPVSSAGGVA IKAGSLIAVL ILRQTNNYNS DDFQFVWNIY ANNDVVVPTG     180
GCDVSARDVT VTLPDYRGSV PIPLTVYCAK SQNLGYYLSG THADAGNSIF TNTASFSPAQ     240
GVGVQLTRNG TIIPANNTVS LGAVGTSAVS LGLTANYART GGQVTAGNVQ SIIGVTFVTQ     300

SEQ ID NO: 6            moltype = AA  length = 279
FEATURE                 Location/Qualifiers
source                  1..279
                        mol_type = protein
                        organism = synthetic construct
SEQUENCE: 6
FACKTANGTA IPIGGGSANV YVNLAPVVNV GQNLVVDLST QIFCHNDYPE TITDYVTLQR      60
GSAYGGVLSN FSGTVKYSGS SYPFPTTSET PRVVYNSRTD KPWPVALYLT PVSSAGGLVI     120
KAGSLIAVLI LRQTNNYNSD DFQFVWNIYA NNDVVVPTGG CDVSARDVTV TLPDYRGSVP     180
IPLTVYCAKS QNLGYYLSGT HADAGNSIFT NTASFSPAQG VGVQLTRNGT IIPTNNTVSL     240
GAVGTSAVSL GLTANYARTG GQVTAGNVQS IIGVTFVYQ                            279

SEQ ID NO: 7            moltype = AA  length = 160
FEATURE                 Location/Qualifiers
source                  1..160
                        mol_type = protein
                        organism = synthetic construct
SEQUENCE: 7
FACKTANGTA IPIGGGSANV YVNLAPVVNV GQNLVVDLST QIFCHNDYPE TITDYVTLQR      60
GSAYGGVLSN FSGTVKYSGS SYPFPTTSET PRVVYNSRTD KPWPVALYLT PVSSAGGLVI     120
KAGSLIAVLI LRQTNNYNSD DFQFVWNIYA NNDVVVPTGG                           160
```